United States Patent [19]
Dershem

[11] Patent Number: 5,861,111
[45] Date of Patent: Jan. 19, 1999

[54] METHOD FOR ISOMERIZATION OF ARYLPROPARGYL ETHER MONOMERS AND USES THEREFOR

[75] Inventor: Stephen M. Dershem, San Diego, Calif.

[73] Assignee: Dexter Corporation, Windsor Locks, Conn.

[21] Appl. No.: 684,148

[22] Filed: Jul. 19, 1996

[51] Int. Cl.$^6$ ..................................................... H01M 4/52
[52] U.S. Cl. ........................... 252/513; 252/511; 252/512
[58] Field of Search ............................. 437/228; 252/511, 252/512, 513

[56] References Cited

U.S. PATENT DOCUMENTS

| | | | |
|---|---|---|---|
| 4,714,569 | 12/1987 | Nishino et al. | 252/511 |
| 5,536,770 | 7/1996 | Glausch et al. | 252/511 |
| 5,605,763 | 2/1997 | Yusa et al. | 252/512 |
| 5,667,899 | 9/1997 | Yusa et al. | 252/512 |

OTHER PUBLICATIONS

Dirlikov and Feng, "Propargyl Terminated Resins. A New Hydrophobic Thermosetting Materials." *3rd International SAMPE Electronics Conference*, 169–180 (1989).

Douglas and Overend, "Curing Reactions in Acetylene Terminated Resins–I. Uncatalyzed Cure of Arylpropargyl Ether Terminated Monomers." *Eur. Polym. J.*, 27(11):1279–1287 (1991).

Harfenist and Thom, "The Influence of Structure on the Rate of Thermal Rearrangement of Aryl Propargyl Ethers to the Chromenes. The gem–Dimethyl Effect." *J. Org. Chem.*, 37(6):841–848 (1972).

Hlubucek et al., "Synthesis of 2,2–Dimethylchromenes." *Tetrahedron Letters*, (17):1369–1370 (1969).

*Primary Examiner*—Amelia Owens
*Attorney, Agent, or Firm*—Gray, Cary, Ware & Freidenrich; Stephen E. Reiter

[57] ABSTRACT

In accordance with the present invention, it has been discovered that arylpropargyl ethers can readily be isomerized to produce benzopyrans, by subjecting a defined group of aryl propargyl compounds to isomerization conditions in suitable solvent. Invention isomerization process allows the production of a good yield of a variety of benzopyran materials, free of contaminating diluent. Benzopyrans prepared in accordance with the present invention are useful for the preparation of adhesive compositions, microelectronic devices, and the like.

12 Claims, No Drawings

METHOD FOR ISOMERIZATION OF ARYLPROPARGYL ETHER MONOMERS AND USES THEREFOR

FIELD OF THE INVENTION

The present invention relates to novel monomeric materials and methods for the preparation thereof, as well as various uses thereof.

BACKGROUND OF THE INVENTION

Cyanate ester resins, epoxy resins and bismaleimide resins comprise the three major classes of thermosetting resins. Thermosetting resins can be used in a wide variety of applications, such as, for example, in the preparation of advanced composite materials, in the preparation of printed circuit board compositions, in the formation of glob-top structures, in a variety of encapsulation applications, in the preparation of adhesive compositions (e.g., die attach compositions), and the like.

Cyanate esters in particular are currently employed for the rapid curing of adhesive compositions used to bond semiconductor devices or chips, also known as dice, to carrier substrates. Such adhesive compositions include, in addition to the cyanate ester, thermally and/or electrically conductive filler, alkylphenol (as a proton donor participating in the cyclotrimerization cure of the cyanate ester monomer), and a curing catalyst dissolved in the alkylphenol.

Cyanate ester adhesive compositions have eliminated many of the deficiencies inherent in epoxy adhesives and polyamide adhesives, such as low glass transition temperature, high degree of ionic contamination, retention of solvent and lengthy cure. Nevertheless, there still remains room for improvement of die attach pastes containing electrically conductive filler in a variety of ways, e.g., by reducing the cost of preparation, by improving the ease of preparation, by improving the working pot life of the preparation, by avoiding the use of potentially detrimental components (e.g., alkylphenols are acidic species, which are potentially corrosive), by avoiding the use of volatile components (which upon cure tend to bleed out, which may lead to the creation of voids in the cured resin), by reducing the propensity of such materials to uptake moisture, by improving the resistance of such materials to hydrolysis, and the like.

BRIEF DESCRIPTION OF THE INVENTION

In accordance with the present invention, it has been discovered that arylpropargyl ethers can readily be isomerized to produce benzopyrans, by subjecting a defined group of aryl propargyl compounds to isomerization conditions in suitable solvent. Invention isomerization process allows the production of a good yield of a variety of benzopyran materials, free of contaminating diluent.

Benzopyrans prepared in accordance with the present invention have surprisingly been found to have substantially enhanced thermal and oxidative stability, relative to the starting materials from which they are prepared. Benzopyrans prepared in accordance with the present invention are useful for a variety of applications, e.g., the preparation of adhesive compositions, microelectronic devices, advanced composite materials, printed circuit board compositions, in the formation of glob-top structures, encapsulation, and the like.

DETAILED DESCRIPTION OF THE INVENTION

In accordance with the present invention, there are provided novel compounds having the structure:

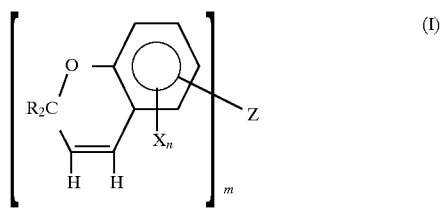

wherein:
X is selected from alkyl, cycloalkyl, alkenyl, alkynyl, alkoxy, halogen, cyano, or the like;

Z, is a di- or trivalent radical capable of linking two or three of the benzopyrene moieties;

each R is independently selected from hydrogen or alkyl having up to 40 carbon atoms;

m is 2 or 3; and n is an integer from 0 up to 3, with the proviso that when X is absent (i.e., n=0), each R is hydrogen, and m=2, Z is not —C(CH$_3$)$_2$—.

As employed herein, the term "alkyl" refers to straight or branched chain alkyl radicals having in the range of about 1 up to 8 carbon atoms, and "lower alkyl" refers to straight or branched chain alkyl radicals having in the range of about 1 up to 4 carbon atoms.

As employed herein, the term "alkenyl" refers to straight or branched chain hydrocarbyl radicals having at least one carbon-carbon double bond, and having in the range of about 2 up to 8 carbon atoms.

As employed herein, the term "alkynyl" refers to straight or branched chain hydrocarbyl radicals having at least one carbon-carbon triple bond, and having in the range of about 2 up to 8 carbon atoms.

As employed herein, the term "alkoxy" refers to an oxygen-bearing alkyl moiety having the structure —OR, wherein R is an alkyl group as defined above.

As employed herein, the term "halogen" refers to fluoride, chloride, bromide or iodide radicals.

Presently preferred compounds of the invention are those wherein:

X is allyl;

Z is selected from:
—O—,
—C(O)—,
—C(O)—O—,
—O—C(O)—O—,
—S—,
—S(O)$_2$—,
—[CR'$_2$]$_x$—, wherein each R' is independently selected from hydrogen, alkyl, fluoroalkyl, cycloalkyl or fluorocycloalkyl, and x is an integer falling in the range of 1 up to 20,
—[O—(CR'$_2$)$_{x'}$]$_y$—O—, wherein each R' is independently as defined above, x' is an integer falling in the range of 1 up to 6, and y is an integer falling in the range of 1 up to 20,
—SiR'$_2$—,
—SiR'$_2$—[—O—SiR'$_2$—]$_{y'}$—, wherein y' is an integer falling in the range of 1 up to 20,

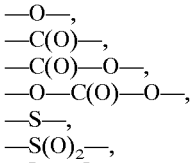

arylene, or cycloalkylene;

R is selected from hydrogen or methyl;

m is 2; and n is an integer from 0 up to 2.

Especially preferred compounds of the invention are those wherein Z is —CHR'—, R' is lower alkyl, m is 2 and n is 0, said compound thereby having the structure:

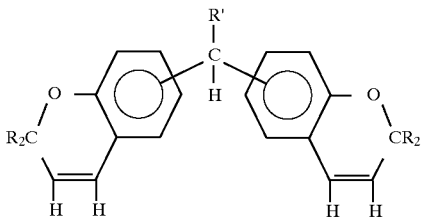
(IV)

wherein each R is independently selected from hydrogen or methyl. A presently preferred compound of the invention is the compound having structure IV, wherein each R is hydrogen and R' is methyl.

In accordance with another embodiment of the present invention, there are provided methods for preparing benzopyran derivatives having the structure I as described hereinabove, said method comprising:

subjecting a dilute solution of a propargyl compound having the structure IIA to isomerization conditions in a suitable low boiling solvent, wherein structure IIA is:

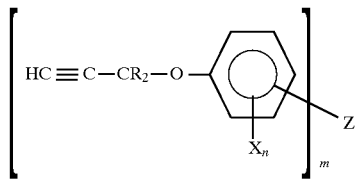
(IIA)

wherein each of R, X, Z, m and n are as defined above,
with the proviso that at least one aryl carbon adjacent to the ether oxygen is not X.

In addition to the above-described method of preparation, there is also provided an alternative method of preparing benzopyran derivatives having the structure I as described hereinabove, said method comprising:

(a) subjecting a dilute solution of a propargyl compound having the structure IIB to isomerization conditions in a suitable low boiling solvent, wherein structure IIB is:

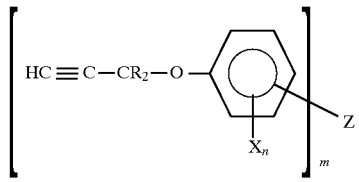
(IIB)

wherein each of X, Z, m and n are as defined above,
with the proviso that at least one aryl carbon adjacent to the ether oxygen is not X, (b) treating the isomerized product produced in step (a) with base under conditions suitable to abstract a hydrogen ion from the methylene moiety of said benzopyran, and concurrently or thereafter (c) contacting the product produced in step (b) with R"—X' under condensation conditions, wherein R" is alkyl and X' is a halogen.

Solvents contemplated for use in the practice of the present invention include $C_4$–$C_8$ aliphatic and/or cycloaliphatic hydrocarbons, chlorinated hydrocarbons, and the like, or mixtures of any two or more thereof. Exemplary solvents include petroleum ethers, cyclohexane, pentanes, hexanes, trimethylpentane, propanes, butanes, dichloromethane, chloroform, carbon tetrachloride, dichloroethylene, methylchloroform, and the like.

The invention isomerization reaction is preferably carried out in dilute solution. Suitable dilute solutions comprise in the range of about 0.5 up to about 5 units by weight of said propargyl compound per 100 volume units of solvent.

Isomerization conditions contemplated for use in the practice of the present invention typically comprise a temperature in the range of about 180° C. up to about 260° C., maintained at a pressure sufficient to maintain the solvent in substantially liquid form. As readily recognized by those of skill in the art, pressures suitable to achieve the desired objective vary as a function of the solvent used, the volume of the reactor used, the capacity of the reactor used, and the like.

The above-described isomerization conditions are maintained for a time sufficient to achieve desired levels of conversion of the propargyl starting material, e.g., typically in the range of about 0.5 up to about 48 hours.

Presently preferred starting materials contemplated for use in the invention synthetic procedure are propargyl compounds having the structure III:

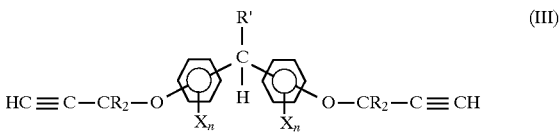
(III)

wherein each of R, R', X and n are as defined above,
with the proviso that at least one aryl carbon adjacent to the ether oxygen is not X.

The above-described method produces bisbenzopyrans having the structure V:

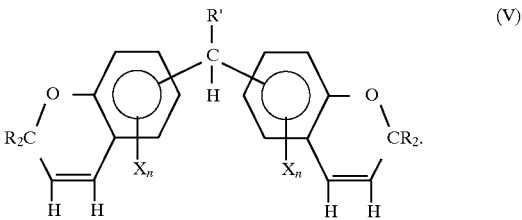
(V)

In accordance with yet another embodiment of the present invention, there are provided compositions for attaching a semiconductor device to a substrate, said compositions comprising:

(i) 8 to 30 wt. percent of a monomer vehicle which is liquid under ambient conditions, and wherein said monomer vehicle is substantially free of added solvent, said monomer vehicle comprising at least one benzopyran having the structure I as described hereinabove;

(ii) 70 to 92 wt. percent of a conductive filler; and (iii) 0.1 to 5 wt. percent of a suitable catalyst.

Presently preferred compositions of the invention are those wherein compound I is defined as follows:

X is allyl;

Z is selected from:
—O—,
—C(O)—,
—S(O)$_2$—,
—[CR'$_2$]$_x$—, wherein each R' is independently selected from hydrogen, alkyl, fluoroalkyl, cycloalkyl or fluorocycloalkyl, and x is an integer falling in the range of 1 up to 20, arylene or cycloalkylene;
R is selected from hydrogen or lower alkyl;
m is 2; and
n is 0 or 1.

Especially preferred compositions of the invention are those wherein compound I is defined as follows: Z is —CHR'—, R' is lower alkyl, m is 2 and n is 0. The resulting benzopyran thereby has the structure IV, as follows:

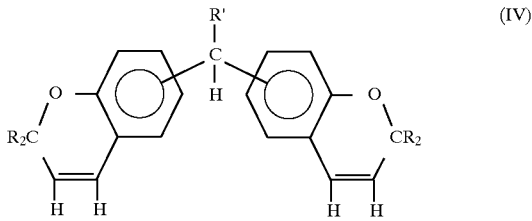

wherein each R is independently selected from hydrogen or methyl. A presently preferred composition of the invention contains compound IV wherein each R is hydrogen and R' is methyl.

Monomer(s) which may be combined with the above-described benzopyrans to produce monomer vehicle is/are selected based on the following criteria: the monomer(s) should be soluble in or miscible with benzopyran monomer and should be non-reactive with benzopyran monomer at ambient temperatures, unless such reaction(s) is(are) reversible at temperatures above ambient temperature.

Monomers that may be combined with benzopyrans in accordance with the present invention are selected from those monomers which undergo addition polymerization. Such monomers include vinyl ethers, divinyl ethers, diallyl ethers, dimethacrylates, dipropargyl ethers, mixed propargyl allyl ethers, monomaleimides, bismaleimides, and the like. Examples of such monomers include trisallylcyanurate, 1,1-bis(4-allyloxyphenyl)ethane, 1,1-bis(4-propargyloxyphenyl)ethane, 1,1-bis(4-allyloxyphenyl-4'-propargyloxyphenyl)ethane, 3-(2,2-dimethyltrimethylene acetal)-1-maleimidobenzene, 2,2,4-trimethylhexamethylene-1,6-bismaleimide, 2,2-bis[4-(maleimidophenoxy)phenyl]propane, and the like.

Various monomers may be combined to obtain a liquid monomer vehicle, without the need for any added solvent/diluent.

Conductive fillers contemplated for use herein include electrically conductive and thermally conductive materials.

Examples of electrically conductive fillers contemplated for use herein include silver, nickel, cobalt, copper, aluminum, metal-coated graphite fibers (e.g., employing such metals as nickel, silver, copper, and the like as the metal coating), and the like, as well as mixtures thereof. The presently preferred electrically conductive filler contemplated for use herein is silver. Both powder and flake forms of filler may be used in the attach paste compositions of the present invention. The preferred thickness of flake is under 2 microns with a dimension of about 20 to about 25 microns. Flake employed herein preferably has a surface area of about 0.15 to 5.0 $m^2/g$ and a tap density of 0.4 to 5.5 g/cc. Powder employed herein preferably has a diameter of about 0.5 to 15 microns.

Thermally conductive fillers contemplated for use in the practice of the present invention include diamond, boron nitride, alumina, aluminum nitride, silicon carbide, magnesium oxide, and the like, as well as mixtures of any two or more thereof.

Catalysts contemplated for use in the practice of the present invention include free radical initiators, cationic catalysts, transition metal catalysts, and the like. Exemplary free radical initiators include peroxy esters, peroxy carbonates, hydroperoxides, alkylperoxides, arylperoxides, and the like.

Exemplary cationic catalysts contemplated for use herein include onium salts, iodonium salts, sulfonium salts, and the like.

Exemplary transition metal catalysts contemplated for use herein include nickel, copper, cobalt and the like, in the form of a chelate, a soap, or the like.

In accordance with still another embodiment of the present invention, there are provided assemblies comprising a microelectronic device permanently adhered to a substrate by a cured aliquot of the above-described composition.

Microelectronic devices contemplated for use in the practice of the present invention include lead frames, pin grid arrays, laminate materials, and the like.

In accordance with a still further embodiment of the present invention, there are provided methods for adhesively attaching a first article to a second article, said method comprising:

(a) applying the above-described composition to said first article, (b) bringing said first and second article into intimate contact to form an assembly wherein said first article and said second article are separated only by the adhesive composition applied in step (a), and thereafter, (c) subjecting said assembly to conditions suitable to cure said adhesive composition.

Conditions suitable for curing the above-described adhesive composition typically comprise a temperature in the range of about 100° up to 250° C., for in the range of about 0.01 up to about 2 hours, with about 0.25 hours curing time being presently preferred.

In accordance with still another embodiment of the present invention, there are provided methods for adhesively attaching a microelectronic device to a substrate, said method comprising:

(a) applying the above-described composition to said substrate and/or said microelectronic device, (b) bringing said substrate and said device into intimate contact to form an assembly wherein said substrate and said device are separated only by the die attach composition applied in step (a), and thereafter, (c) subjecting said assembly to conditions suitable to cure said die attach composition.

Conditions suitable for curing the above-described adhesive composition typically comprise a temperature in the range of about 100° up to 250° C., for in the range of about 0.01 up to about 2 hours, with about 0.25 hours curing time being presently preferred.

As readily recognized by those of skill in the art, compositions according to the present invention can also be employed for the preparation of advanced composites, molding resins, glob-top structures, underfill materials, and the like, employing techniques which are readily available in the art.

The invention will now be described in greater detail by reference to the following non-limiting examples.

EXAMPLE 1

Five and one half grams (5.5 g) of the propargyl ether having Structure III, wherein each R is H and R' is methyl, was placed in an empty 500 ml round bottom flask, along with 20 mg of butylated hydroxytoluene (BHT). Decane (149 g) was then added along with some boiling stones. The reaction mixture was then blanketed with argon and refluxed for about 63 hours. The reaction mixture was then allowed to cool to room temperature and passed through fine filter paper. The paper absorbed all of the colored impurities.

A small aliquot of the clear decane solution was evaporated. The clear, oily residue was dissolved in acetone and a portion of this solution was then evaporated onto an attenuated reflectance cell for Fourier transform infrared spectroscopy (FTIR). The most notable difference in the isomerized product relative to the starting material was the reduction in intensity of the alkynyl absorption (at 2387 $cm^{-1}$), intensification of C—H stretches (perhaps due to residual solvent), and the appearance of new absorption peaks at 1636, 1489, and 891 wave numbers (i.e., $cm^{-1}$).

EXAMPLE 2

Five and one half grams (5.5 g) of the propargyl ether employed in Example 1 was dissolved in 100 g of tripropyleneglycol monomethyl ether (which has a boiling point of 236° C.). This solution was then refluxed for about 4 hours. The reaction contents were then cooled and 80 ml of pentane added thereto. The solution was placed in a separatory funnel and washed twice with 100 ml aliquots of water, followed by two washes with 40 ml aliquots of water containing 1% potassium hydroxide. Finally, the pentane solution was washed three times with water, dried over magnesium sulfate and solvent removed on the rotary evaporator. The resulting product was a moderately viscous oil. FTIR showed the complete disappearance of the 3287 and 2102 wave number absorbances (characteristic of alkynyl moieties), along with strong absorption at 1504 wave numbers (which also disappears), while the 1489 wave number absorption (characteristic of benzopyran) became quite large. 2.3 g of oily product was obtained after removing the pentane.

EXAMPLE 3

Ten grams (10 g) of the propargyl ether employed in Example 1 was added to a 500 ml boiling flask along with boiling chips, 200 ml of dodecane, and about 34 ml of methoxy phenol. The reaction mixture was allowed to reflux for about 8 hours under a nitrogen purge. The vessel contents were then allowed to cool to room temperature. The resulting liquid phase was somewhat turbid and sticky. The sticky component was readily removed by filtration through 0.45 $\mu$m filter disks. The filtrate was then swirled with about 1 g of inhibitor remover, then with 1 g of decolorizing carbon, and finally with 2 g of Celite. The solids were then removed by gravity filtration. The filtrate was then extracted 6 times with 50 ml aliquots of acetonitrile. The combined acetonitrile washes were then rinsed twice with 30 ml aliquots of pentane, then the solvent removed by rotary evaporation to yield 5.24 g of a yellow oil. This product appeared, by FTIR, to be substantially free of any uncyclized propargyl ether starting material.

EXAMPLE 4

Seven and one half grams (7.5 g) of p-cumylpropargyloxy benzene (i.e., the propargyl ether of p-cumylphenol), 200 ml of dodecane and 30 mg of BHT was subjected to reflux for about 8.5 hours under a nitrogen atmosphere. The resulting yellow solution was then allowed to cool to room temperature, and was passed over neutral alumina for decolorization. The resulting dodecane solution was then extracted 13 times with 20 ml aliquots of acetonitrile. The collected acetonitrile extracts were then washed once with 20 ml of pentane. The acetonitrile phase was then concentrated by rotary evaporation to yield a low viscosity yellow oil.

EXAMPLE 5

Five grams (5 g) of p-cumylpropargyloxy benzene, 200 ml of hexane and 27 mg of BHT were loaded into a glass-lined pressure vessel. A magnetic stirbar was added to the pressure vessel, which was then sealed and purged with argon. The reaction mixture was then heated to about 250° C. and maintained for about 3 hours. The reaction mixture was then allowed to cool to room temperature and the resulting yellow liquid was decolorized over alumina, then concentrated by rotary evaporation under a nitrogen sparge. FTIR showed the isomerization reaction to be essentially complete.

EXAMPLE 6

Ten grams (10 g) of p-cumylpropargyloxy benzene, 30 mg of BHT, and 200 ml of hexane were introduced into a glass-lined pressure vessel. The contents of the reaction vessel were then heated in a controlled temperature bath to about 230° C. (which generated a pressure of about 300 psig). The reaction temperature of 230° C. was maintained for about 7 hours, then an FTIR was run on the residue, which showed that the desired isomerization was not yet complete.

The reactor contents were sparged with argon, then heated again, this time up to about 245° C. (which generated a pressure of about 325 psig). Reaction was then continued for an additional 4+ hours, for a total reaction time of about 11+ hours. FTIR analysis of the resulting reaction mixture showed that the isomerization was substantially complete. The resulting orange solution was then decolorized over neutral alumina and then evaporated, producing about 3.1 g of yellow oil.

EXAMPLE 7

Seven and one half grams (7.5 g) of p-cumylpropargyloxy benzene, 30 mg of BHT, and 300 ml of hexane were loaded into a glass-lined pressure vessel. The vessel contents were then heated in a temperature bath maintained at about 232° C. (generating a pressure in the range of about 310–335 psig). After about 6.5 hours reaction time, FTIR revealed that isomerization was incomplete. Isomerization was then continued for an additional 4.5 hours (for a total reaction time of about 11 hours), at which time FTIR indicated that conversion was essentially complete.

Greater than 60% yield of the desired product was obtained after removal of hexane solvent by rotary evaporation. Thus, conducting the desired isomerization reaction in dilute solution (e.g., using 7.5 g of starting material in 300 ml of solvent) is seen to provide a dramatic increase in product yield, relative to results obtained in other reactions employing a higher concentration of starting material.

EXAMPLE 8

Seven and one half grams (7.5 g) of p-cumylpropargyloxy benzene, 30 mg of BHT, and 300 ml of hexane were introduced into a glass-lined pressure vessel. Isomerization was conducted at a temperature of about 250° C. (which generated a pressure of about 420 psig). A sample was removed from the reaction vessel about 3.25 hours after the reaction temperature had been reached, and analyzed by FTIR. After this amount of reaction time, the desired isomerization was determined to be incomplete. The isomerization was then continued at about 250° C. for an additional 2 hours, at which time isomerization was deemed to be complete. The recovered yield for this process was about 39%.

Based on additional iterations of the above-described reaction under a variety of conditions, the yield for reaction carried out at lower temperature (i.e., at about 230° C.) for a longer reaction time (i.e., about 11–12 hours) was seen to provide substantially higher yield of the desired isomerization product than was achieved at elevated temperature for reduced reaction time.

While the invention has been described in detail with reference to certain preferred embodiments thereof, it will be understood that modifications and variations are within the spirit and scope of that which is described and claimed.

That which is claimed is:

1. A composition for attaching a semiconductor device to a substrate, said composition comprising:
   (i) 8 to 30 wt. percent of a monomer vehicle which is liquid under ambient conditions, wherein said monomer vehicle is substantially free of added solvent, said monomer vehicle comprising at least one benzopyrene moiety having the structure:

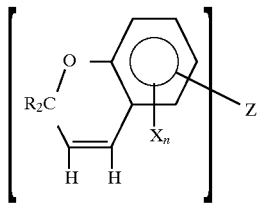

(I)

wherein:
   X is selected from alkyl, cycloalkyl, alkenyl, alkynyl, alkoxy, halogen, or cyano;
   Z is a di- or trivalent radical capable of linking the benzopyrene moiety;
   each R is independently selected from hydrogen or alkyl having up to 40 carbon atoms;
   m is 2 or 3; and
   n is an integer from 0 up to 3,
   (ii) 70 to 92 wt. percent of a conductive filler; and
   (iii) 0.1 to 5 wt. percent of a suitable catalyst.

2. A composition according to claim 1 wherein Z is —CHR'—, wherein R' is lower alkyl, m is 2 and n is 0, said benzopyran thereby having structure V as follows:

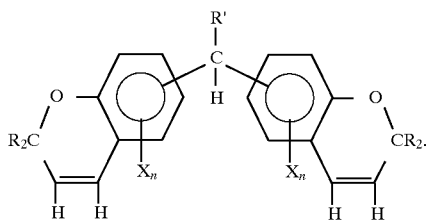

(V)

wherein R is hydrogen or methyl.

3. A composition according to claim 1 wherein said conductive filler is electrically conductive.

4. A composition according to claim 3 wherein said electrically conductive filler is selected from silver, nickel, cobalt, copper, aluminum, metal-coated graphite fibers, or mixtures thereof.

5. A composition according to claim 3 wherein said filler is silver.

6. A composition according to claim 3 wherein said conductive filler is thermally conductive.

7. A composition according to claim 6 wherein said thermally conductive filler is selected from diamond, boron nitride, alumina, aluminum nitride, silicon carbide, magnesium oxide, or mixtures of any two or more thereof.

8. A composition according to claim 1 wherein said suitable catalyst is a free radical initiator or a cationic catalyst.

9. A composition according to claim 8 wherein said free radical initiator is selected from peroxy esters, peroxy carbonates, hydroperoxides, alkylperoxides or arylperoxides.

10. A composition according to claim 8 wherein said cationic catalyst is selected from onium salts, iodonium salts or sulfonium salts.

11. A composition according to claim 1 wherein said monomer vehicle further comprises additional monomer selected from the group consisting of vinyl ethers, divinyl ethers, diallyl ethers, dipropargyl ethers, propargyl allyl ethers, monomaleimides, bismaleimides, acrylates, methacrylates, styrenes, and mixtures of any two or more such monomers.

12. A composition according to claim 1 wherein:
   X is allyl;
   Z is divalent and selected from:
      —C(O)—,
      —C(O)—O—,
      —O—C(O)—O—,
      —S—,
      —S(O)$_2$—,
      —(CR'$_2$)$_x$—, wherein each R' is independently selected from hydrogen, alkyl, fluoroalkyl, cycloalkyl or fluorocycloalkyl, and x is an integer falling in the range of 1 up to 20,
      —(O—(CR'$_2$)$_{x'}$)$_y$—O—, wherein each R' is independently as defined above, x' is an integer falling in the range of 1 up to 6, and y is an integer falling in the range of 1 up to 20,
      —SiR'$_2$—,
      —SiR'$_2$—(—O—SiR'$_2$—)$_{y'}$—, wherein y' is an integer falling in the range of 1 up to 20,
      —NR'—,
      arylene, or
      cycloalkylene;
   R is selected from hydrogen or methyl;
   m is 2; and
   n is an integer from 0 up to 2.

* * * * *